US005362744A

United States Patent [19]

Purchase, Jr. et al.

[11] Patent Number: 5,362,744

[45] Date of Patent: Nov. 8, 1994

[54] TETRAZOLE-SUBSTITUTED UREA ACAT INHIBITORS

[75] Inventors: Claude Forsey Purchase, Jr., Ann Arbor; Andrew D. White, Lakeland, both of Mich.

[73] Assignee: Warner-Lambert Company, Morris Plains, N.J.

[21] Appl. No.: 156,128

[22] Filed: Nov. 22, 1993

[51] Int. Cl.[5] .................... C07D 257/06; A61K 31/41

[52] U.S. Cl. .................................... 514/381; 514/382; 548/251; 548/253

[58] Field of Search ................ 548/251, 253; 514/381, 514/382

[56] References Cited

U.S. PATENT DOCUMENTS

| | | | |
|---|---|---|---|
| 5,015,644 | 5/1991 | Roth et al. | 514/247 |
| 5,073,565 | 12/1991 | Chucholowski et al. | 514/381 |

*Primary Examiner*—Joseph Paul Brust

*Assistant Examiner*—Mary Susan H. Gabilan

*Attorney, Agent, or Firm*—Michael J. Atkins; Charles W. Ashbrook

[57] ABSTRACT

Novel ACAT inhibitors useful in the treatment of atherosclerosis which are tetrazole-substituted ureas,

23 Claims, No Drawings

TETRAZOLE-SUBSTITUTED UREA ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain novel compounds which inhibit the enzyme acylcoenzyme A: cholesterol acyltransferase (ACAT), pharmaceutical compositions containing these compounds, and a method of treating hypercholesterolemia and atherosclerosis.

In recent years the roles which elevated blood plasma levels of cholesterol play in pathological conditions in man has received much attention. Deposits of cholesterol in the vascular system have been indicated as causative of a variety of pathological conditions including coronary heart disease.

Initially, studies of this problem were directed toward finding therapeutic agents which could be effective in lowering total serum cholesterol levels. It is now known that cholesterol is transported in the blood in the form of complex particles consisting of a core of cholesteryl esters plus triglycerides and an exterior consisting primarily of phospholipids and certain apolipoproteins which are recognized by specific receptors. For example, cholesterol is carried to the sites of deposit in blood vessel in the form of low-density lipoprotein cholesterol (LDL cholesterol) and away from such sites of deposit by high-density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall..

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT also effectively inhibit the intestinal absorption of dietary cholesterol into the blood stream or the reabsorption of cholesterol which has been previously released into the intestine through the body's own regulatory action.

INFORMATION DISCLOSURE STATEMENT

*Chemical Abstracts* 1972:76:25184v reports the synthesis of N-phenyl-N'-(1-phenyl-1H-tetrazol-5-yl)-urea. No utility for the compound is given.

*J. Medicinal Chemistry* 1979;22:28–32 reports antileukemic data for N-(4-ethoxycarbonylphenyl)-N'-tetrazol-5-yl-urea.

U.S. Pat. No. 5,073,565, issued Dec. 17, 1991, and related Patent Cooperation Treaty Application 91/02959, filed Apr. 25, 1991, and published Nov. 14, 1991, disclose tetrazole urea and thiourea ACAT inhibitors of the following formula:

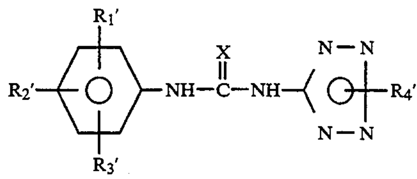

The tetrazole-substituted urea ACAT inhibitors of the present invention are not taught by these references. Moreover, the tetrazole-substituted urea ACAT inhibitors of the present invention have been found to be characterized as nontoxic in in vivo studies. The nontoxic nature of the compounds of the present invention is particularly advantageous.

International Patent Application PCT/EP91/01341, filed Jul. 18, 1991, discloses compounds having selective $LTB_4$ antagonist properties and comprising an aryl or heteroaryl mono- or bicyclic ring which has at least two substituents attached thereto; (1) a substituted or unsubstituted aryl or heteroaryl monoor bicyclic ring and (2) a substituent chain having a terminal carboxylic acid functional group or derivative thereof attached thereto. This invention further relates to processes for their preparation and therapeutic compositions comprising said compound and methods for the treatment of disorders involving $LTB_4$agonist-mediated activity utilizing said compositions wherein the compounds are described by the following general formula and pharmaceutically acceptable salts thereof:

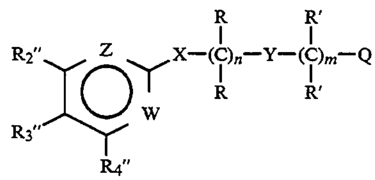

SUMMARY OF INVENTION

The present invention provides a class of compounds which have acyl-CoA:cholesterol acyltransferase (ACAT) inhibitory activity and intermediates useful in preparing said compounds having the following structure:

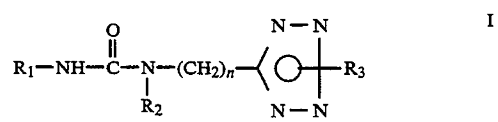

I wherein $R_1$ is phenyl which is unsubstituted or is substituted with from 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms; wherein $R_2$ is (a) aryl which is unsubstituted or substituted with 1 to 3 substituents selected from fluorines chlorine, bromine, iodine, hydroxy, a straight or branched alkyl group having from 1 to 6 carbon atoms, or a straight or branched alkoxy group having from 1 to 6 carbon atoms;

(b) a straight or branched hydrocarbon group which is saturated or contains from 1 to 3 double bonds and having from 1 to 20 carbon atoms and wherein said group is unsubstituted or is substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

(c) a straight or branched alkoxy group which is saturated or contains from 1 to 3 double bonds and having from 1 to 20 carbon atoms and wherein said group is unsubstituted or is substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

(d) a cycloalkyl group having from 3 to 8 atoms which is unsubstituted or substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms; or (e) aralkyl wherein an aromatic group is attached to a straight or branched alkyl group having from 1 to 4 carbon atoms and which is unsubstituted or is substituted on the aromatic ring with from 1 to 3 substituents selected from fluorine, chlorine, bromine, iodine, hydroxy, a straight or branched alkyl group having from 1 to 6 carbon atoms or a straight or branched alkoxy group having from 1 to 6 carbon atoms;

wherein $R_3$ is attached to either the 1- or 2-position of the tetrazole ring and is selected from a straight or branched hydrocarbon chain having from 1 to 20 carbon-atoms and which is saturated or unsaturated containing 1 double bond or 2 or 3 nonadjacent double bonds wherein said chain is unsubstituted or is substituted with from 1 to 6 substituents selected from:

(a) —$NR_4R_5$ wherein each of $R_4$ and $R_5$ is the same or different and is hydrogen, a straight or branched alkyl group having from 1 to 20 carbon atoms or —$NR_4R_5$ taken together form a monocyclic heterocyclic group selected from pyrrolidino, pyridino, piperidino, piperazino, or morpholino, the heterocyclic group being unsubstituted or substituted with a straight or branched alkyl group having from 1 to 4 carbon atoms;

(b) $OR_6$ wherein $R_6$ is hydrogen, a straight or branched alkyl group having from 1 to 20 carbon atoms or a cycloalkyl group having from 3 to 8 carbon atoms or phenyl which is unsubstituted or substituted with from 1 to 3 substituents selected from fluorine, chlorine, bromine, iodine, hydroxy, a straight or branched alkyl group having from 1 to 6 carbon atoms, or a straight or branched alkoxyalkyl group having from 1 to 6 carbon atoms;

(c) $SO_2R_6$ wherein $R_6$ has the meaning defined above;

(d) $SOR_6$ wherein $R_6$ has the meaning defined above;

(e) $SR_6$ wherein $R_6$ has the meaning defined above;

(f) $COR_6$ wherein $R_6$ has the meaning defined above;

(g) $CO_2R_6$ wherein $R_6$ has the meaning defined above;

(h) $CONR_4R_5$ wherein $R_4$ and $R_5$ have the meanings defined above;

(i) $CONHR_1$ wherein $R_1$ has the meaning defined above;

(j) —CHO (k) —CN (l) halogen (m) the group —$(CH_2)$ r-phenyl wherein r is 1 to 4 and the phenyl moiety is unsubstituted or is substituted with from 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms; or (n) O-pyranyl which is unsubstituted or substituted with from 1 to 4 substituents selected from fluorine, chlorine, bromine, iodine, hydroxy, a straight or branched alkyl group having from 1 to 6 carbon atoms, or a straight or branched alkoxy group having from 1 to 6 carbon atoms;

and n=0, 1, or 2;

a geometrical or optical isomer, or a pharmaceutically acceptable salt thereof.

DETAILED DESCRIPTION OF THE INVENTION

The present invention provides a novel class of compounds which contain a tetrazole moiety and which are ACAT inhibitors rendering them useful in treating hypercholesterolemia and atherosclerosis. As used herein, "halogen" means fluorine, chlorine, bromine, and iodine. "Aryl" is intended to mean any stable monocyclic, bicyclic, or tricyclic carbon ring of up to 7 members in each ring, wherein at least 1 ring is aromatic. Examples of such aryl elements include, but are not limited to, phenyl, naphthyl, tetrahydronapthyl, or biphenyl.

Illustrative examples of straight or branched hydrocarbon chains having from 1 to 20 carbon atoms and having 1 double bond which the group $R_3$ may represent include ethenyl, 2-propenyl, 2-butenyl, 3-pentenyl, 2-octenyl, 5-nonenyl, 4-undecenyl, 5-heptadecenyl, 3-octadecenyl, 9-octadecenyl and hexadecenyl, or having 2 nonadjacent double bonds which the group $R_3$ may represent include 9,12-octadecadienyl.

Illustrative examples of straight or branched saturated hydrocarbon chains having from 1 to 20 carbon atoms, include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative examples of straight or branched hydrocarbon chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadencenyl, 3-octadecenyl, 9-octadecenyl, 2,2-dimethyl-11-eicosenyl, 9,12-octadecadienyl, and hexadecenyl.

Straight or branched alkoxy groups having from 1 to 4 carbon atoms as used herein include, for example, methoxy, ethoxy, n-propoxy, t-butoxy, or having from 1 to 6 carbon atoms include, for example, additionally n-pentyloxy, 3-ethylpropoxy, 5-methylpentyloxy, and n-hexyloxy.

Illustrative examples of straight or branched alkyl groups having from 1 to 4 carbon atoms as used herein include methyl, ethyl, n-propyl, isopropyl, n-butyl, tert-butyl or having from 1 to 6 carbon atoms include additionally n-pentyl, 2-methylbutyl, 4-methylpentyl, n-hexyl, and 5-methylpentyl.

Preferred compounds of this invention are those of general Formula I wherein $R_1$ is substituted phenyl and more preferred are those wherein $R_1$ is di- or trisubstituted phenyl, and even more preferred are those compounds where $R_1$ is 2,6—, 2,4—, or 2,4,6-substituted phenyl.

Most preferably, $R_1$ is 2,6-diisopropylphenyl, 2,4,6-trimethoxyphenyl, 2,4-difluorophenyl, or 2,4,6-trifluorophenyl.

Preferred compounds of this invention are also those of general Formula I wherein $R_2$ is phenyl substituted with alkyl, alkoxy, or halogen. In another embodiment it is preferred that where $R_2$ is a lower straight or branched chain alkyl that $R_2$ is $—(CH_2)_6CH_3$, or where $R_2$ is cycloalkyl that $R_2$ is cyclohexyl or where $R_2$ is aralkyl that $R_2$ is benzyl. Most preferred compounds are those of general Formula I wherein $R_2$ is phenyl or cyclohexyl.

Preferred compounds of this invention are also those of general Formula I wherein $R_3$ is an alkyl chain of from about 11 to 14 carbon atoms, such as 2-dodecyl, 2-tetradecyl, and -8-[(tetrahydro-2H-pyran- 2-yl)oxy]-octyl.

Most preferred compounds of the present invention, and pharmaceutical compositions comprised of the most preferred compounds of the present invention include, but are not limited to, the following:

N'-[2,6-bis(1-methylethyl)phenyl]-N-(2-dodecyl-2H-tetrazol-5-yl)-N-phenyl-urea,

N-(2-dodecyl-2H-tetrazol-5-yl)-N-phenyl-N'-(2,4,6-trimethoxyphenyl )-urea,

N'-(2,4-difluorophenyl)-N-(2-dodecyl-2H-tetrazol-5-yl)-N-phenyl-urea,

N'-[2,6-bis(1-methylethyl)phenyl]-N-cyclohexyl-N-(2-dodecyl-2H-tetrazol-5-yl)-urea, N-cyclohexyl-N-(2-dodecyl-2H-tetrazol-5-yl)-N'-(2,4,6-trimethoxyphenyl)-urea, N-cyclohexyl-N-(2,4-difluorophenyl)-N-(2-dodecyl-2H-tetrazol-5-yl)-urea, N-phenyl-N-(2-tetradecyl-2H-tetrazol-5-yl)-N'-(2,4,6-trimethoxyphenyl)-urea, N-(2-pentyl-2H-tetrazol-5-yl)-N-phenyl-N'-(2,4,6-trimethoxyphenyl)-urea, N-(2-dodecyl-2H-tetrazol-5-ylmethyl)-N-(phenyl methyl)-N'-(2,4,6-trimethoxyphenyl)-urea, (±)N'-[2,6-bis(1-methylethyl)phenyl]-N-phenyl-N-[2-[8-[(tetrahydro-2H-pyran-2-yl)oxy]octyl]-2H-tetrazol-5-yl]-urea, (±)N-phenyl-N-[2-[8-[(tetrahydro-2H-pyran-2-yl)oxy]octyl]-2H-tetrazol-5-yl]-N'-(2,4,6-trimethoxyphenyl)-urea, (±)N'-(2,4-difluorophenyl)-N-phenyl-N-[2-[8-[(tetrahydro-2H-pyran-2-yl)oxy]octyl]-2H-tetrazol-5-yl]-urea, N'-[2,6-bis(1-methylethyl)phenyl]-N-[2-(8-hydroxyoctyl)-2H-tetrazol-5-yl]-N-phenyl-urea, N-[2-(8-hydroxyoctyl)-2H-tetrazol-5-yl]-N- phenyl-N'-(2,4,6-trimethoxyphenyl)-urea, N'-[2,6-bis(1-methylethyl)phenyl]-N-[2-(8-oxooctyl)-2H-tetrazol-5-yl]-N-phenyl-urea, N-[2-(8-oxooctyl)-2H-tetrazol-5-yl]-N-phenyl-N'-(2,4,6-trimethoxyphenyl)-urea, or N'-[2,6-bis(1-methylethyl)phenyl]-N-[2-[8-(diethylamino)octyl]-2H-tetrazol-5-yl]-N-phenyl-urea.

Pharmaceutically acceptable salts of the compounds of Formulas I and II are also included in the scope of the present invention.

The acid salts may be generated from the free base by reaction of the latter with 1 equivalent of a suitable nontoxic, pharmaceutically acceptable acid, followed by evaporation of the solvent employed for the reaction and recrystallization of the salt, if required. The free base may be recovered from the acid salt by reaction of the salt with an aqueous solution of a suitable base such as sodium carbonate, sodium bicarbonate, potassium carbonate, sodium hydroxide, and the like.

Suitable acids for forming acid salts of the compound of this invention include, but are not necessarily limited to acetic, benzoic, benzene-sulfonic, tartaric, hydrobromic, hydrochloric, citric, fumaric, fluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well-known to practitioners of the pharmaceutical formulation arts (see, for example, Berge SN, et al., *J. Pharm, Sciences,* 1977;66:1–19).

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solrated forms with pharmaceutically acceptable solvents such as water, ethanol, and the like. In general, the solvated forms are considered equivalent to the unsolvated forms for the purposes of this invention.

As shown by the data presented below in Table I, the compounds of the present invention are potent inhibitors of the enzyme acyl-CoA: cholesterol acyl-transferase (ACAT), and are thus effective in inhibiting the esterification and transport of cholesterol across liver and arterial cell walls. The compounds of the present invention are also potent inhibitors of liver and arterial ACAT, and are thus effective in inhibiting very low-density lipids (VLDL) secretion from the liver and foam cell formation within the arterial wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field FJ, Salone RG, *Biochemica et Biophysica,* 1982;712:557–570. The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table I where they are expressed in $IC_{50}$ values; i.e., the concentration of test compound required to inhibit the activity of the enzyme by 50%.

TABLE I

| Example | LAI $IC_{50}$ (μM) |
|---|---|
| 1 | 0.047 |
| 2 | 0.061 |
| 3 | 0.24 |
| 4 | 0.031 |
| 5 | 0.057 |
| 6 | 0.34 |
| 7 | 0.071 |
| 8 | 0.45 |
| 9 | 0.053 |
| 10 | 0.016 |
| 11 | 0.041 |
| 12 | 0.10 |
| 13 | 0.99 |
| 14 | >5.0 |

TABLE I-continued

| Example | LAI $IC_{50}$ (μM) |
|---|---|
| 15 | 0.85 |
| 16 | 7.1 |
| 17 | 1.5 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with the PCC diet (5.5% peanut oil, 1.5% cholesterol, and 0.5% cholic acid). The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table II wherein percent change means the difference in total cholesterol between control, and the drug-treated animals.

TABLE II

| Example | APCC (%ΔTC) 30 mg/kg |
|---|---|
| 1 | −52 |
| 2 | −74 |
| 3 | −63 |
| 4 | −10 |
| 5 | −67 |
| 6 | −33 |
| 7 | −22 |
| 8 | −43 |
| 9 | −49 |
| 10 | −42 |
| 11 | −50 |
| 12 | −37 |
| 13 | −17 |
| 14 | −15 |
| 15 | −29 |
| 16 | −8 |
| 17 | −30 |

As indicated above, and shown by the data presented below, the compounds of the present invention have been found to be characterized as nontoxic in in vivo studies conducted. The nontoxic nature of the compounds of the present invention is particularly advantageous and surprising in light of toxicity screens of previously disclosed tetrazole urea ACAT inhibitors, but which are not substituted at the alpha-position. The compounds of the present invention are thus useful in pharmaceutical formulations for the treatment of hypercholesterolemia or atherosclerosis.

The nontoxic nature of representative compounds of the present invention was measured and compared against previously disclosed tetrazole urea ACAT inhibitors using an in vivo toxicity screen developed by Dominick, et al., 1993. Male guinea pigs of the Hartley strain (450–500 g) were obtained from Charles River and randomly divided into treatment groups. They were fed standard guinea pig chow ad libitum and dosed daily (AM) by gavage (100 mg/kg). The test compounds were dissolved or suspended in an oleic acid vehicle to facilitate absorption. After 2 weeks the animals were sacrificed by $CO_2$ asphyxiation in the nonfasted state 16 hours after the last dose. Adrenal glands were weighed, fixed in 10% formalin, processed by routine paraffin techniques, sectioned, and then stained with hematoxylin and eosin for light microscopy. Toxicity was defined by the incidence, severity, and complexity of adrenal histopathologic alterations in the zona fasciculata (e.g., adrenal cortical atrophy, increased coarse vacuolation, single cell necrosis, inflammatory cell infiltrates, mineralization/ectopic bone formation, and increased cytoplasmic eosinophilia).

The results indicated that previously disclosed tetrazole urea compound, N-[2,6-bis(1-methylethyl)-phenyl]-N'-(2-dodecyl-2H-tetrazol-5-yl)-urea is classed as highly toxic to the adrenal gland. Cytotoxic zonal atrophy of the zona fasciculata (near complete loss of zona fasciculata due to cortical cell necrosis and degeneration) in 3/6 treated animals. Necrosis of the adrenal cortex was observed in 2/6 animals and inflammatory cell infiltrates were present in 2/6 animals. Increased coarse vacuoles were present in 5/6 animals.

The results further indicated that previously disclosed tetrazole urea, N-[2,6-bis(1-methylethyl)-phenyl]-N'-(2-tridecyl-2H-tetrazol-5-yl)-urea is classed as highly toxic to the adrenal gland. Cytotoxic zonal atrophy of the zona fasciculata (near complete loss of zona fasciculata due to cortical cell necrosis and degeneration) in 4/6 treated animals. Necrosis of the adrenal cortex was observed in 3/6 animals and inflammatory cell infiltrates were present in 2/6 animals. Increased coarse vacuoles were present in 5/6 animals.

The results, however, did show that the test compound of the present invention, N-cyclohexyl-N-(2-dodecyl-2H-tetrazol-5-yl)-N'-(2,4,6-trimethoxyphenyl)-urea is classed as nontoxic to the adrenal gland, exhibiting no drug related adrenal changes.

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations included powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methylcellulose, sodium carboxymethylcellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methylcellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention can be prepared by various routes, all of which are generally known in the art. The compounds of Formula I wherein n is O, $R_2$ is aryl, and $R_1$ and $R_3$ are as defined in Formula I can be prepared as set forth in Chart I hereof.

In Chart I, the thiourea (1) of formula $R_2NHCSNH_2$, wherein $R_2$ is as defined in Formula I, is converted to the isothiourea hydroiodide (2) by alkylation with an alkyl iodide wherein the alkyl iodide is typically methyl iodide or ethyl iodide. The isothiourea hydroiodide (2) is converted to the aminoguanidine hydroiodide (3) by reaction with hydrazine in a suitable solvent such as ethanol or methanol at temperatures between 0° C. and reflux. The aminoguanidine hydroiodide (3) is converted to the 5-amino-1-aryltetrazole (4) by treatment with silver nitrate in a suitable solvent system, such as dilute nitric acid in water or dilute nitric acid in a water/t-butanol mixture, at temperatures typically between 25° C. and 50° C. followed by filtration to remove the halide as its silver salt, and then reaction with an alkali metal nitrite such as sodium or potassium nitrite at temperatures between 0° C. and 25° C. The 5-amino-1-aryltetrazole (4) is isomerized to the N-aryltetrazol-5-amine (5) by heating in a solvent such as toluene or xylenes at reflux. The tetrazole (5) is converted to a mixture of the 2- and 1-alkylated aminotetrazole isomers (6) and (7), respectively, by reaction with an alkyl halide of the formula $R_3$ halo wherein $R_3$ has the meaning as defined in Formula I and halo is iodine, bromine, or chlorine, in a suitable solvent such as acetonitrile containing a tertiary amine base, typically triethylamine or diisopropylethylamine, at temperatures between 25° C. and reflux. The aminotetrazoles (6) and (7) can be separated by chromatography and then independently converted to the corresponding 2- and 1-tetrazole-substituted ureas (8) and (9), respectively, by reaction with n-butyl lithium in tetrahydrofuran at −78° C. followed by triphosgene at temperatures between −78° C. and reflux followed by an amine of the formula $R_1NH_2$, wherein $R_1$ has the meaning as defined in Formula I at temperatures between 25° C. and reflux. Alternatively, the aminotetrazoles (6) and (7) can be converted to the corresponding ureas (8) and (9), respectively, by reaction with sodium hydride and triphosgene together in tetrahydrofuran at temperatures between 0° C. and reflux followed by an amine of the formula $R_1NH_2$, by reaction with phosgene in toluene or dichloromethane in the presence of a suitable amine base such as triethylamine or diisoproplethylamine at temperatures between 0° C. and reflux followed by an amine of the formula $R_1NH_2$, or by reaction with n-butyl lithium in tetrahydrofuran at −78° C. followed by an isocyanate of the formula $R_1NCO$, wherein $R_1$ has the meaning as defined in Formula I.

The thioureas of Formula I are either commercially available or can be synthesized by employing the following reaction sequence:

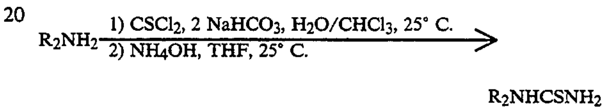

$$R_2NH_2 \xrightarrow[\text{2) } NH_4OH,\ THF,\ 25^\circ\ C.]{\text{1) } CSCl_2,\ 2\ NaHCO_3,\ H_2O/CHCl_3,\ 25^\circ\ C.} R_2NHCSNH_2$$

Compounds of Formula I wherein n is 0, $R_2$ is cyclohexyl, and $R_1$ and $R_3$ are as defined in Formula I are synthesized employing the sequence illustrated in Chart II. In Chart II, the phenylamino tetrazoles (10) and (13), prepared as described above, are converted to the cyclohexylamino tetrazoles (11) and (14), respectively, by hydrogenation using appropriate conditions, such as 1000 psi of hydrogen over 10% ruthenium catalyst on carbon in ethanol at 100° C. The cyclohexylamino tetrazoles (11) and (14) are then converted to the ureas (12) and (15), respectively, by sequential reaction with phosgene in toluene or triphosgene in tetrahydrofuran in the presence of suitable bases such as diisopropylethylamine, sodium hydride, or n-butyl lithium followed by an appropriate amine of the formula $R_1NH_2$, wherein $R_1$ has the meaning defined in Formula I, and a suitable base such as diisopropylethylamine.

Compounds of Formula I wherein n is 0, $R_2$ is cycloalkyl, alkyl, or aralkyl, and $R_1$ and $R_3$ are as defined in Formula I are synthesized employing the sequence illustrated in Chart III. In Chart III, 5-aminotetrazole monohydrate (16) is converted to a mixture of the 2- and 1-substituted tetrazole regioisomers (17) and (18), respectively, by alkylation with $R_3$ halo wherein $R_3$ has the meaning defined in Formula I and halo is iodine, bromine, or chlorine. The 2- and 1-substituted regioisomers can be separated by chromatography and independently deprotonated and alkylated with $R_2$ halo wherein $R_2$ has the meaning defined in Formula I and halo is iodine, bromine, or chlorine to provide the aminotetrazoles (19) and (20), respectively. The aminotetrazoles (19) and (20) are converted to the ureas (21) and (22), respectively, by sequential reaction with n-butyl lithium in tetrahydrofuran at −78° C., triphosgene, and then an amine of the formula $R_1NH_2$, wherein $R_1$ has the meaning defined in Formula I, and a suitable base such as diisopropylethylamine.

Compounds of Formula I wherein n is 1 or 2, and $R_1$, $R_2$, and $R_3$ are as defined in Formula I are synthesized employing the sequence illustrated in Chart IV. In Chart IV, either ethyl cyanoformate (23, n=1) or ethyl cyanoacetate (23, n=2) are reacted with an alkali metal azide, such as lithium or sodium azide, in a mixture of trifluoroacetic acid and pyridine at 60° C. to provide the tetrazole esters (24). The tetrazole esters (24) are converted to the 2- and 1-substituted tetrazole esters (25) and (26), respectively, by alkylation with $R_3$ halo wherein $R_3$ has the meaning defined in Formula I and halo is iodine, bromine, or chlorine. The mixture of the 2- and 1-substituted regioisomers (25) and (26) can be separated by chromatography and independently hydrolyzed to the 2- and 1-substituted tetrazole carboxylic acids (27) and (28), respectively. The carboxylic acids (27) and (28) can be coupled with an appropriate amine $R_2NH_2$, wherein $R_2$ has the meaning as defined in Formula I, using coupling reagents such as 1,1'-carbonyldiimidazole, or N,N'-dicyclohexylcarbodiimide, to give the tetrazole amides (29) and (30), respectively. The amides (29) and (30) are converted to the aminotetrazoles (31) and (32), respectively, by reduction using a hydride reducing agent such as lithium aluminum hydride in diethyl ether or tetrahydrofuran at temperatures of 0° C. to 56° C. The aminotetrazoles (31) and (32) are converted to the ureas (33) and (34), respectively, by sequential reaction with phosgene in toluene and diisopropylethylamine as a base followed by an amine of the formula $R_1NH_2$ wherein $R_1$ has the meaning as defined in Formula I, and a suitable base such as diisopropylethylamine.

Compounds of Formula I wherein $R_3$ is substituted alkyl and n, $R_1$, and $R_2$ are as defined in Formula I may be synthesized as previously described for Charts I, III, and IV. Alternatively, some of the compounds of Formula I wherein $R_3$ is substituted alkyl may be synthesized by employing a strategy of interconverting suitable compounds that fall within the scope of Formula I following the sequences illustrated in Chart V. For example in Chart V, the O-tetrahydropyranyl ureas (35) and (39), wherein substituent $R_6$ is as defined in Formula I, are hydrolyzed to the alcohols (36) and (40) under mild acidic conditions in an aqueous alcohol, such as a catalytic amount of 4-methylbenzenesulfonic acid in 95% methanol at room temperature. The alcohols (36) and (40) are converted to either the corresponding aldehydes (37, $R_6$=H) and (41, $R_6$=H) or ketones (37, $R_6$ is alkyl) and (41, $R_6$ is alkyl) by oxidation using suitable conditions, such as pyridinium chlorochromate at 25° C. in dichloromethane containing a buffer such as anhydrous sodium acetate. The aldehydes (37, $R_6$=H) and (41, $R_6$=H) and ketones (37, $R_6$ is alkyl) and (41, $R_6$ is alkyl) are converted to the amines (38) and (42), wherein $R_4$ and $R_5$ are as defined in Formula I, by condensation with an amine of formula $HNR_4R_5$, wherein $R_4$ and $R_5$ are as defined in Formula I, in an anhydrous alcohol containing a catalytic amount of an acid, such as hydrogen chloride in methanol, followed by reduction of the intermediate with a suitable hydride donor, such as sodium cyanoborohydride or sodium borohydride.

Some of the compounds of Formula I wherein $R_3$ is substituted alkyl and n, $R_1$, and $R_2$ are as defined in Formula I, may be synthesized by employing a strategy of interconverting suitable compounds that fall within the scope of Formula I following the sequences illustrated in Chart VI. In Chart VI, the alcohol (36, $R_6$=H) is oxidized to the carboxylic acid (43) by reaction with a suitable oxidizing agent such as chromium trioxide in acetone. The carboxylic acid (43) is converted to the ester (44) by reaction with an alcohol of the formula $R_6OH$, wherein the group $R_6$ is as defined in Formula I, under mild conditions such as a catalytic amount of 4-methylbenzenesulfonic acid in refluxing benzene with a Dean-Stark trap to remove water or with 3 Angstrom molecular sieves in benzene at room temperature. The carboxylic acid (43) can also be converted to the amide (45) by reaction with a coupling reagent such as 1,1'-carbonyldiimidazole in tetrahydrofuran or N,N'-dicyclohexylcarbodiimide in dichloromethane followed by an amine of the formula $HNR_4R_5$, wherein $R_4$ and $R_5$ are as defined in Formula I. The carboxylic acid (43) can also be converted to the amide (46) by reaction with one of the coupling agents followed by an amine of the formula $R_1NH_2$, wherein $R_1$ is as defined in Formula I. The corresponding 1-substituted tetrazole carboxylic acid, ester, and amides can be prepared from the alcohol (40, $R_6$=H) following the sequences described above.

Some of the compounds of Formula I wherein $R_3$ is substituted alkyl and n, $R_1$, and $R_2$ are as defined in Formula I, may be synthesized by employing a strategy of interconverting suitable compounds that fall within the scope of Formula I following the sequences illustrated in Chart VII. In Chart VII, the alcohol (36*a*, $R_6$=H) is converted to the bromide (47) by reaction with a suitable halogenating agent such as phosphorous tribromide or thionylbromide in a solvent such as dichloromethane at temperatures between 0° C. and 40° C. The bromide (47) can then be converted either to the nitrile (48) by reaction with sodium cyanide in dimethylsulfoxide at temperatures between 25° C. and 95° C. or to the sulfide (49) by reaction with a thiol of the formula $R_6SH$ in the presence of a suitable base, such as sodium hydride or diisopropylethylamine, in a solvent such as dimethylformamide at temperatures between 0° C. and 95° C., wherein $R_6$ has the meaning as defined in Formula I. The sulfide (49) can be converted to the racemic sulfoxide (50) by reaction with a suitable oxidizing agent such as sodium metaperiodate in aqueous alcohol such as 95% methanol at temperatures between −25° C. and 25° C. Alternatively, the sulfide (49) can be converted to either enantiomer of the racemic sulfoxide (50) by reaction with the appropriate form of a chiral oxidizing agent, such as (+) or (−) 8,8-dichlorocamphorylsulphonyloxaziridine in a solvent such as toluene at temperatures between 25° C. and 50° C. The sulfoxide (50) can be converted to the sulfone (51) by reaction with an appropriate oxidizing agent such as 30% hydrogen peroxide in glacial acetic acid at temperatures between 25° C. and reflux. The corresponding 1-substituted tetrazole bromide, nitrile, sulfide, sulfoxide, and sulfone can be prepared from the alcohol (40, $R_6$=H) following the sequences described above.

The amines of formulas $R_1NH_2$ and $R_2NH_2$, wherein $R_1$ and $R_2$ have the meanings defined in Formula I, employed in preparing compounds of this invention, are known in the art or can be prepared by procedures generally known in the art.

The halides of formulas $R_2$ halo and $R_3$ halo, wherein $R_2$ and $R_3$ have the meanings defined in Formula I employed in preparing compounds of this invention, are known in the art or can be prepared by procedures generally known in the art.

The following specific examples further illustrate the invention.

EXAMPLE 1

N'-[2,6-Bis(1-methylethyl)phenyl]-N-(2-dodecyl-2H-tetrazol-5-yl)-N-phenyl-urea ($R_1$=2,6-diisopropylphenyl; $R_2$=phenyl; n=0; $R_3$=2-$(CH_2)_{11}CH_3$).

(a) Phenyl-carbamimidothioic acid, methyl ester, monohydroiodide

To a stirred, chilled (+3° C.) suspension of phenylthiourea (15.66 g, 0.1029 mol) in absolute ethanol under nitrogen atmosphere was added in one portion methyl iodide (6.4 mL, 0.10 mol), and the mixture was stirred for 1.5 hours. The suspension was allowed to warm to room temperature over 1.5 hours and was stirred. All of the solids dissolved within 5 hours at room temperature to give a yellow solution. After 6 hours a thick off-white precipitate formed. After 40 hours diethyl ether (400 mL) was added dropwise. The solids were filtered off, washed with diethyl ether, and dried in vacuo (25° C.), yield 28.26 g (97%), mp=142°-144° C.

(b) N'-Phenyl-hydrazinecarboximidamide monohydroiodide

To a stirred room temperature suspension of phenylcarbamimidothioic acid, methyl ester, monohydroiodide (91.5 g, 0.311 mol) in absolute ethanol (280 mL) was added in one portion anhydrous hydrazine (9.8 mL, 0.31 mol), and the mixture was heated to reflux. The mixture was refluxed for 3 hours and allowed to cool. The resulting solution was purged with nitrogen to remove methanethiol and rotary evaporated to an oil. The oil was dried in vacuo briefly then dissolved in water (130 mL). The solution was rotoevaporated to an oil. The oil was dried in vacuo (50° C.), yield 87.08 g (100%). $^1$H NMR (DMSO-$d_6$): δ 9.5 (br s, 0.5H), 9.0 (br s, 1.5H), 7.7 (br s, 2H), 7.4 (t, 2H), 7.2 (m, 3H), 4.8 (br s, 2H).

(c) 1-Phenyl-1H-tetrazol-5-amine

To a warm (50° C.), stirred solution of N'-phenylhydrazinecarboximidamide monohydroiodide (86.4 g, 0.31 mol) in water (300 mL) was added in one portion 70% nitric acid (2.80 mL, 0.0435 mol) followed by dropwise addition of a solution of silver nitrate (52.66 g, 0.3100 mol) in water (70 mL). The resulting suspension was allowed to cool over 30 minutes. To the still warm (+35° C.) mixture was added concentrated hydrochloric acid (3.6 mL). The solids were filtered off and washed with hot water (60 mL). The filtrate and washings were combined and acidified with concentrated hydrochloric acid (22.3 mL). The mixture was chilled (+5° C.) and stirred while a solution of sodium nitrite (21.46 g, 0.3110 mol) in water (70 mL) was added dropwise. The temperature of the solution was kept below 8° C. by controlling the addition rate. The solution was stirred for 15 minutes. To the mixture was added powdered sodium carbonate (36.14 g, 0.341 mol) in small portions to avoid excessive foaming. The resulting precipitate was stirred for 2 days. The solids were filtered off, washed with water (3×20 mL), and dried under house vacuum/air bleed at 45° C.; yield 38.77 g (77.4%), mp=158.5°-159.5° C.

(d) N-Phenyl-1H-tetrazol-5-amine

A suspension of 1-phenyl-1H-tetrazol-5-amine (38.63 g, 0.2397 mol) in xylenes (380 mL) was refluxed under nitrogen for 1.3 hours and allowed to cool. The suspension was stirred overnight. The mixture was chilled (+3° C.) for 2 hours, and the solids were filtered off. The filter cake was washed with PET ether and then dissolved in a solution of potassium hydroxide (20.1 g, 0.358 mol) in water (1.1 L). The mixture was filtered, and the filtrate was acidified by the dropwise addition of concentrated hydrochloric acid (46 mL, 0.55 mol). A precipitate formed. The solids were filtered off, washed with water (25 mL), and dried under house vacuum/air stream (40° C.), yield 35.0 g h(90%); mp=208°-209° C. (gas evol.)

(e) 2-Dodecyl-N-phenyl-2H-tetrazol-5-amine and 1-Dodecyl-N-phenyl-1H-tetrazol-5-amine A stirred solution of Nophenyl-1H-tetrazol-5-amine (21.03 g, 0.1305 mol), 1-bromododecane (31.5 mL, 0.13 mol), and triethylamine (20 mL, 0.14 mol) in acetonitrile (400 mL) was refluxed under nitrogen atmosphere for 15 hours and allowed to cool. The mixture was rotoevaporated, and the residue was triturated with diethyl ether. The diethyl ether was rotoevaporated, and the residue was chromatographed on silica gel (1.4 kg, 230-400 mesh) using PET ether-ethyl acetate (9:1, 6×1 L; 6:1, 4×1 L; 2:1, 10×1 L) as eluent. Fractions containing the front-running isomer were rotoevaporated from $CH_2Cl_2$ to give a pale yellow oil which solidified upon standing. The solid was dried in vacuo to give 2-dodecyl-N-phenyl-2H-tetrazol-5-amine, yield 30.0 g (70%), mp=58°-61° C.

Fractions containing trailing isomer were rotoevapoarated to a pale yellow solid, yield 2.57 g (6.0%) of 1-dodecyl-N-phenyl-1H-tetrazol-5-amine, mp=108°-111° C.

(f) N'-[2.6-Bis(1-methylethyl)phenyl]-N-(2-dodecy-2H-tetrazol-5-yl)-N-phenyl-urea To a stirred, cold (−78° C.) solution of 2-dodecyl-N-phenyl-2H-tetrazol-5-amine (2.2 g, 0.0067 mol) in anhydrous tetrahydrofuran (30 mL) under nitrogen atmosphere was added dropwise a 2.5 M solution of n-butyl lithium in hexanes (2.7 mL, 0.0068 mol), and the mixture was stirred for 25 minutes. To the mixture was added triphosgene (0.6385 g, 0.002152 mol) in one portion. The mixture was stirred for 1.5 hours and then allowed to warm to room temperature. The resulting orange solution was stirred for 3 days. To the mixture was added diisopropylethylamine (1.3 mL, 0.0069 mol) and 2,6-bis(1-methylethyl)aniline (1.3 mL, 0.0069 mol), and the mixture was refluxed for 3 days. The reaction mixture was allowed to cool and then rotoevaporated. The residue was partitioned between diethyl ether and saturated sodium bicarbonate. The organic layer was washed with additional saturated sodium bicarbonate, 1M hydrochloric acid, saturated sodium chloride, and was dried over magnesium sulfate. The organics were rotoevaporated to an oil. The oil was dissolved in PET ether and chromatographed on silica gel (360 g, 230-400 mesh) using PET ether-ethyl acetate (15:1, 3×300 mL; 11:1, 20×350 mL) as eluent. Fractions containing product were rotoevaporated from dichloromethane and dried in vacuo (50° C.), yield 2.798 g (78%) of the title compound. $^1$H NMR ($CDCl_3$): δ 9.3 (s, 1H), 7.5 (m, 6H), 7.2 (d, 2H), 4.5 (t, 2H), 3.2 (septet, 2H), 1.9 (m, 2H), 1.2 (m, 18H), 0.9 (t, 3H).

EXAMPLE 2

N-(2-Dodecyl-2H-tetrazol-5-yl)-N-phenyl-N'-(2,4,6-trimethophenyl)-urea

In a manner similar to Example 1, 2-dodecyl-N-phenyl-2H-tetrazol-5-amine was reacted with triphosgene and 2,4,6-trimethoxyaniline hydrochloride in the presence of two equivalents of diisopropylethylamine to give the title compound. $^1$H NMR (DMSO): δ 8.3 (s, 0.25H), δ 8.2 (s, 0.75H), 7.4 (m, 2H), 7.3 (m, 3H), 6.2 (s, 2H), 4.6 (t, 2H), 3.8 (s, 3H), 3.7 (s, 6H), 1.9 (m, 2H), 1.2 (m, 18H), 0.9 (t, 3H) .

EXAMPLE 3

N'-(2,4-Difluorophenyl)-N-(2-dodecyl-2H-tetrazol-5-yl)-N-phenyl-urea

In a manner similar to Example 1, 2-dodecyl-N-phenyl-2H-tetrazol-5-amine was reacted with triphosgene and 2,4-difluoroaniline to give the title compound, mp=55°-57° C.

EXAMPLE 4

N'-2,6-Bis(1-methylethyl)phenyl]-N-cyclohexyl-N-(2-dodecyl-2H-tetrazol-5-yl)-urea (a) N-Cyclohexyl-2-dodecyl-2H-tetrazol-5-amine A mixture of 2-dodecyl-N-phenyl-2H-tetrazol-5-amine (1.54 g, 0.00467 mol) and absolute ethanol (100 mL) was hydrogenated over 10% ruthenium on carbon (0.5 g) at 1100 psi and 100° C. for 10 hours. The mixture was allowed to cool to room temperature, and the catalyst was filtered off and washed with additional ethanol (200 mL). The filtrate and washings were combined and rotoevaporated to a glaze. The glaze was triturated with diethyl ether. The organic triturate was rotoevaporated to a solid, and the solid chromatographed on silica gel (50 g, 70-230 mesh) using PET ether-acetone (10:1, 7×50 mL) as eluent. Fractions containing title compound were rotoevaporated from dichloromethane to a white solid. The solid was dried in vacuo (25° C.), yield 1.30 g (83%), mp=51°-53° C.

(b) N'-[2,6-Bis(1-methylethyl)phenyl]-N-cyclohexyl-N-(2-dodecvl-2H-tetrazol-5-yl)-urea A suspension of a 60% dispersion of sodium hydride in mineral oil (0.2648 g, 0.0066 mol) in a solution of triphosgene (0.4583 g, 0.001544 mol) and N-cyclohexyl-2-dodecyl-2H-tetrazol-5-amine (1.5540 g, 0.0046313 mol) in anhydrous tetrahydrofuran (15 mL) under a nitrogen atmosphere was refluxed for 4.5 days. To the mixture was added 2,6-bis(1-methylethyl)aniline (0.88 mL, 0.0047 mol) and diisopropylethylamine (0.89 mL, 0.0051 mol), and the reflux was continued for 7 days. The mixture was rotoevaporated, and the residue partitioned between diethyl ether and saturated sodium bicarbonate. The organic layer was washed with 1M hydrochloric acid and saturated sodium chloride, dried ($MgSO_4$), and rotoevaporated to an oil. The oil was chromatographed on silica gel (430 g, 230-400 mesh) using PET ether-ethyl acetate (30:1, 14×400 mL) to give the title compound as an oil, yield 1.4522 g (58%) . $^1$H NMR ($CDCl_3$): δ 8.8 (s, 1H), 7.3 (dd, 2H), 7.2 (d, 1H), 4.6 (m, 3H), 3.1 (septet, 2H), 2.1 (m, 4H), 1.8 (m, 4H), 1.6 (m, 2H), 1.3 (m, 32H), 0.9 (t, 3H).

EXAMPLE 5

N-Cyclohexyl-N-(2-dodecyl-2H-tetrazol-5-yl)-N'-(2,4,6-trimethoxyphenyl)-urea In a manner similar to Example 4, N-cyclohexyl-2-dodecyl-2H-tetrazol-5-amine was condensed with triphosgene and 2,4,6-trimethoxyaniline hydrochloride in the presence of two equivalents of diisopropylethylamine to give the title compound. $^1$H NMR ($CDCl_3$): δ 8.5 (s, 1H), 6.2 (s, 2H), 4.6 (m, 1H), 4.5 (t, 2H), 3.8 (s, 9H), 2.0 (m, 4H), 1.8 (m, 4H), 1.6 (m, 2H), 1.3 (m, 20H), 0.8 (t, 3H).

EXAMPLE 6

N-Cyclohexyl-N'-(2,4-difluorophenyl)-N-(2-dodecyl-2H-tetrazol-5-yl)-urea

To a stirred mixture of N-cyclohexyl-2-dodecyl-2H-tetrazol-5-amine (0.3349 g, 0.0009981 mol) and diisopropylethylamine (1.7 mL, 0. 0098 mol) at room temperature under nitrogen atmosphere was added a 12.5 wt/wt % solution of phosgene in toluene (8 mL). The mixture was heated at 45° C. for 22 hours and allowed to cool. Excess phosgene was removed, and the mixture was rotoevaporated to a sludge. The residue was suspended in anhydrous tetrahydrofuran (25 mL), additional diisopropylethylamine (0.35 mL, 0. 0020 mol) and 2,4-difluoroaniline (0.11 mL, 0.0011 mol) were added, and the mixture was refluxed for 6 days. The mixture was partitioned between diethyl ether and 1M hydrochloric acid. The organic layer was washed with saturated sodium chloride, dried ($Na_2SO_4$), and rotoevaporated to an oil. The oil was chromatographed twice on silica gel: (80 g, 230-400 mesh) using PET ether-acetone (7:1) and (68 g, 230-400 mesh) using PET ether-acetone (40:1) to give the title compound as a yellow oil, yield 0.2995 g (61%). $^1$H NMR ($CDCl_3$): δ 9.9 (s, 1H) , 8.2 (m, 1H) , 6.9 (m, 2H), 4.6 (m, 3H), 2.1 (m, 4H), 1.8 (m, 4H), 1.6 (m, 2H), 1.3 (m, 20H), 0.9 (t, 3H).

EXAMPLE 7

N-Phenyl-N-(2-tetradecyl-2H-tetrazol-5-yl)-N'-(2,4,6-trimethoxyphenyl)

When in the procedure of Example 1(e) an appropriate amount of 1-bromotetradecane was substituted for 1-bromododecane and the general procedures of 1(e) and (f) were followed, the title compound was obtained. $^1$H NMR ($CDCl_3$): δ 8.7 (s, 1H), 7.4 (m, 5H), 6.2 (s, 2H), 4.5 (t, 2H), 3.8 (2s, 9H), 2.0 (m, 2H), 1.3 (m, 22H), 0.9 (t, 3H).

EXAMPLE 8

N-(2-Pentyl-2H-tetrazol-5-yl)-N-phenyl-N'-(2,4,6-trimethophenyl)-urea

When in the procedure of Example 1(e) an appropriate amount of 1-bromopentane was substituted for 1-bromododecane and the general procedures of 1(e) and (f) were followed, the title compound was obtained, mp=115°-116 ° C.

EXAMPLE 9

N-(2-Dodecyl-2H-tetrazol-5-ylmethyl)-N-(phenylmethyl)-N'-(2,4,6-trimethoxyphenyl)-urea (a) 1H-Tetrazole-5-carboxylic acid, ethyl ester To a stirred, room temperature solution of ethyl cyanoformate (19.57 g, 0.1975 mol) in pyridine (78 mL) was added a chilled (+5° C.) mixture of trifluoroacetic acid (33 mL) and pyridine (118 mL) followed by sodium azide (14.06 g, 0.2163 mol), and the mixture was heated at 60° C. for 46 hours. The mixture was allowed to cool, poured into a mixture of concentrated hydrochloric acid (180 mL) and ice (400 g), and extracted with ethyl acetate several times. The extracts were washed with saturated sodium chloride, dried ($MgSO_4$), and rotoevaporated to an oil. The oil was chromatographed on silica gel (500 g, 70-230 mesh) using ethyl acetatemethanol (15:1, 10×1 L) as eluent. Fractions containing product were rotoevaporated to an oil. The oil was dissolved in chloroform, filtered to remove a precipitate, and the filtrate extracted with aqueous sodium hydroxide. The extracts were acidified to pH 1 and extracted with ethyl acetate. The extracts were dried ($MgSO_4$) and rotoevaporated to a white solid, yield 1.91 g (7%) of the title compound, mp=87.5°-91.5° C.

(b) 2-Dodecyl-2H-tetrazole-5-carboxylic acid, ethyl ester and 1-Dodecyl-1H-tetrazole-5-carboxylic acid, ethyl ester When in the manner of Example 1(e), an appropriate amount of 1H-tetrazole-5-carboxylic acid, ethyl ester was substituted for N-phenyl-1H-tetrazol-5-amine, and the general procedure is followed the title compounds are obtained. The 2-substituted isomer was obtained as a white solid, mp=41°-45° C. The 1-substituted isomer was obtained as an oil. $^1$H NMR ($CDCl_3$): δ 4.7 (t, 2H), 4.6 (q, 2H), 2.0 (m, 2H), 1.5 (t, 3H), 1.2-1.4 (m, 18H), 0.9 (t, 3H).

(c) 2-Dodecyl-2H-tetrazole-5-carboxylic acid

To a room temperature, stirred solution of potassium hydroxide (1.97 g, 0.035 mol) in absolute ethanol (280 mL) was added in one portion 2-dodecyl-2H-tetrazole-5-carboxylic acid, ethyl ester (8.7 g, 0.028 mol), and the mixture was stirred for 28 hours. A white precipitate formed. The solids were filtered off, washed with ethanol, and partitioned between ethyl acetate and 10% hydrochloric acid. The organic layer was washed with saturated sodium chloride, dried ($MgSO_4$), and rotoevaporated to a white solid, yield 7.74 g (98%), mp=122°-124° C.

(d) 2-Dodecyl-N,(phenylmethyl)-2H-tetrazole-5-carboxamide

To a stirred, room temperature solution of 2-dodecyl-2H-tetrazole-5-carboxylic acid (8.00 g, 0.0283 mol) in anhydrous tetrahydrofuran (80 mL) under a nitrogen atmosphere was added in one portion 1,1'-carbonyldiimidazole (4.96 g, 0.0306 mol),and the mixture was stirred. A thick suspension formed. After 2 hours benzylamine (3.3 mL, 0.030 mol) was added in one portion, and the mixture was stirred. The solids dissolved. After 3 days a precipitate was filtered off and set aside. The filtrate was rotoevaporated, and the residue was dissolved in diethyl ether. The solution was washed with 1M sodium hydroxide solution, 1M hydrochloric acid, saturated sodium chloride, and dried ($Na_2SO_4$). The solution was rotoevaporated to give the title compound as a white solid, yield 7.06 g (67%), mp=58°-64° C.

(e) 2-Dodecyl-N-(phenylmethyl)-2H-tetrazole-5-methanamine

To a stirred, room temperature suspension of lithium aluminum hydride (0.6633 g, 0.01748 mol) in dry diethyl ether (35 mL) was added dropwise a cloudy solution of 2-dodecyloN-(phenylmethyl)-2H-tetrazole-5-carboxamide (6.50 g, 0.0175 mol) in diethyl ether (35 mL) and tetrahydrofuran (15 mL) under a nitrogen atmosphere over 1 hour. The mixture was then heated at reflux and stirred. After 2.5 days, the mixture was allowed to cool, chilled to +5° C., and quenched with water (0.7 mL). A 4.36M solution (0.7 mL) of sodium hydroxide in water was added followed by additional water (2 mL). The resulting suspension was filtered off through celite, and the filtrate was rotoevaporated to an oil. The oil was chromatographed on silica gel (300 g, 230-400 mesh) using PET ether-ethyl acetate (3:1, 15×250 mL) as eluent. Fractions containing product were rotoevaporated and dried in vacuo to give the title compound as a pale yellow oil, yield 2.93 g (47%). $^1$H NMR ($CDCl_3$): δ 7.3 (m, 5H), 4.6 (t, 2H), 4.1 (s, 2H), 3.9 (s, 2H), 2.0 (br s, 3H), 1.1-1.4 (m, 18H), 0.9 (t, 3H).

(f) N-(2-Dodecyl-2H-tetrazol-5-ylmethyl)-N-(phenyl methyl)-N'-(2,4,6-trimethoxyphenyl)-urea When in the procedure of Example 6 appropriate amounts of 2-dodecyl-N-(phenylmethyl)-2H-tetrazole-5-methanamine and 2,4,6-trimethoxyaniline were substituted for N-cylcohexyl-2-dodecyl-2H-tetrazol-5-amine and 2,4-difluoroaniline, respectively, the title compound was obtained, mp=57°-59° C.

EXAMPLE 10

(±)N'-[2,6-Bis(1-methylethyl)phenyl]-N-[phenyl-N-[2-[8-[(tetrahydro-2H-pyran-2-yl)oxy]octal]-2H-tetrazol-5-yl]-urea (a) (±)2-[(8-Bromooctyl)oxy]tetrahydro-2H-pyran To a stirred, room temperature suspension of Amberlyst 15 resin (2.37 g) in a solution of 8-bromo-1-octanol (9.50 g, 0.0454 mol) in heptane (95 mL) was added dropwise neat 3,4-dihydro-2H-pyran (5.0 mL, 0.055 mol) under a nitrogen atmosphere, and the mixture was stirred for 22 hours. The resin was filtered off, and the filtrate was rotoevaporated to an oil. The oil was chromatographed on silica gel (400 g, 230-400 mesh) using PET ether-diethyl ether (10:1, 10×500 mL) as eluent. Fractions containing title compound were rotoevaporated and dried in vacuo to give a clear, colorless oil, yield 10.92 g (82%). $^1$H NMR ($CDCl_3$): δ 4.6 (dd, 1H), 3.9 (m, 1H), 3.8 (m, 1H), 3.5 (m, 1H), 3.4 (m, 3H), 1.8 (m, 3H), 1.7 (m, 1H), 1.6 (m, 6H), 1.4 (m, 1H), 1.3 (m, 7H).

(b) (±)N-Phenyl-2-[8-[(tetrahydro-2H-pyran-2-yl)oxy]-octal]-2H-tetrazol-5-amine and (±) N-phenyl-1-[8 [(tetra-hydro-2H-pyran-2-yl) oxy]octal]-1H-tetrazol-5-amine A mixture of N-phenyl-1H-tetrazol-5-amine (5.9102 g, 0.036671 mol), (±)2[(8-bromooctyl)oxy]tetra-hydro-2H-pyran (10.75 g, 0.03666 mol), and triethylamine (5.60 mL, 0.0402 mol) in acetonitrile (200 mL) was refluxed under a nitrogen atmosphere for 2.5 days. The solvent was rotoevaporated and the residue was triturated with diethyl ether. The triturate was rotoevaporated, and the residue chromatographed on silica gel (393 g, 230-400 mesh) using PET ether-acetone (6:1, 20×400 mL) as eluent. Fractions containing front-running product were rotoevaporated from chloroform to give a yellow oil. The oil was dried in vacuo, wherein it crystallized, yield 9.25 g (68%) of the 2-substituted isomer, mp=69°-71° C.

Fractions containing trailing isomer were rotoevaporated from chloroform and dried in vacuo to give a white solid, yield 2.52 g (18%) of the 1-substituted isomer, mp=88°-92° C.

(c)

(±)N'-[2,6-Bis(1-methylethyl)phenyl-N-phenyl-N-[2-[8-[(tetrahydro-2H-pyran-2-yl)oxy]octyl]-2H-tetrazol-5-yl]-urea When in the procedure of Example 1(f) an appropriate amount of (±)N-phenyl-2-[8-[(tetrahydro-2H-pyran-2-yl)oxy]octyl]-2H-tetrazol-5-amine was substituted for 2-dodecyl-N-phenyl-2H-tetrazol-5-amine, the title compound was obtained. $^1$H NMR ($CDCl_3$): δ 9.3 (br s, 0.75H) , 9.2 (br s, 0.25H), 7.5 (t, 2H), 7.4 (m, 3H), 7.3 (d, 1H), 7.2 (d, 2H), 4.6 (m, 1H), 4.5 (t, 2H), 3.9 (m, 1H), 3.8 (m, 1H), 3.5 (m, 1H), 3.4 (m, 1H), 3.2 (septet, 2H), 2.0 (m, 2H), 1.5–1.8 (m, 10H), 1.3 (br s, 6H), 1.2 (d, 12H).

EXAMPLE 11

(±)N-Phenyl-N-[2-[8-[(tetrahydro-2H-pyran-2-yl)oxy]-octyl]-2H-tetrazol-5-yl]-N'-(2,4.6-trimethoxyphenyl)-urea When in the procedure of Example 1(f) an appropriate amount of (±)N-phenyl-2-[8-[(tetrahydro-2H-pyran-2-yl)oxy]octyl]-2H-tetrazol-5-amine was substituted for 2-dodecyl-N-phenyl-2H-tetrazol-5-amine, and reacted with triphosgene and 2,4,6-trimethoxyaniline hydrochloride in the presence of two equivalents of diisopropylethylamine, the title compound was obtained. $^1$H NMR ($CDCl_3$): 8.7 (br s, 0.6H), 8.6 (br s, 0.4H), 7.4 (m, 5H), 6.2 (s, 2H), 4.6 (m, 1H), 4.5 (m, 2H), 3.8 (two s, 9H), 3.7 (m, 1H), 3.6 (t, 1H), 3.5 (m, 1H), 3.4 (m, 1H), 1.9 (m, 2H), 1.7–1.9 (m, 6H), 1.6 (m, 4H), 1.3 (m, 6H).

EXAMPLE 12

(±)N'-(2,4-Difluorophenyl)-N-phenyl-N-[2-[8-[(tetrahydro-2H-pyran-2-yl)oxy]octyl]-2H-tetrazol-5-yl]-urea To a stirred, cold (−78° C.) solution of (±)N-phenyl-2-[8-[(tetrahydro-2H-pyran-2-yl) oxy]octyl]-2H-tetrazol-5-amine (0.6161 9, 0.001650 mol) in anhydrous tetrahydrofuran (20 mL) was added a 1.6M solution of n-butyl lithium in hexanes (1.0 mL, 0.0016 mol) under a nitrogen atmosphere, and the mixture was stirred. After 2.5 hours, 2,4-difluorophenyl isocyanate (0. 195 mL, 0. 00165 mol) was added dropwise, and the mixture was stirred. After 3 hours the mixture was allowed to warm to room temperature and then stirred 1.5 days. The mixture was poured into water and extracted with ethyl acetate. The organic layer was washed with saturated sodium chloride, dried ($Na_2SO_4$), and rotoevaporated to an oil. The oil was chromatographed on silica gel (120 g, 230–400 mesh) using chloroform-diethyl ether (24:1, 13×100 mL) as eluent. Fractions containing product were rotoevaporated from diethyl ether to give the title compound as a yellow oil. The oil was dried in vacuo, yield 0.5406 g (64%). $^1$H NMR (CDC13): δ 10.4 (br s, 1H), 8.3 (m, 1H), 7.5 (m, 3H), 7.4 (d, 2H), 6.9 (m, 2H), 4.6 (m, 1H), 4.5 (t, 2H), 3.9 (m, 1H), 3.7 (m, 1H), 3.5 (m, 1H), 3.4 (m, 1H), 2.0 (m, 2H), 1.5–1.9 (m, 9H), 1.3 (m, 7H).

EXAMPLE 13

N'-[2,6-Bis(1-methylethyl)phenyl]-N-[2-(8-hydroxyoctyl)-2H-tetrazol-5-yl]-N-phenyl-urea To a stirred, room temperature solution of (±)N'-[2,6-bis(1-methylethyl)phenyl-N-phenyl-N-[2-[8-[(tetrahydro-2H-pyran-2-yl)oxy]octyl]-2H-tetrazol-5-yl]-urea (2.1600 g, 0.0037449 mol) in methanol (20 mL) was added dropwise water (1.0 mL) and 4-methylbenzenesulfonic acid monohydrate (0.0594 g, 0.000312 mol), and the mixture was stirred. After 46 hours the mixture was rotoevaporated, and the residue was chromatographed on silica gel (230 g, 230–400 mesh) using PET ether-diethyl ether (1:2, 15×200 mL) as eluent. Fractions containing product were rotoevaporated from dichloromethane to an oil. The oil was dried in vacuo (95° C., 15 min; 17h, 25° C.) to give the title compound, yield 1.482 g (80%). $^1$H NMR ($CDCl_3$): δ 9.2 (br s, 1H), 7.5 (t, 2H), 7.4 (m, 3H), 7.3 (d, 1H), 7.2 (d, 2H), 4.5 (t, 2H), 3.6 (t, 2H), 3.2 (septet, 2H), 2.0 (m, 2H), 1.5 (m, 4H), 1.3 (m, 6H), 1.2 (d, 12H).

EXAMPLE 14

N-[2-(8-hydroxyoctyl)-2H-tetrazol-5-yl]-N-phenyl-N'-(2,4,6-trimethoxyphenyl)-urea In a manner similar to Example 13, (±)N-phenyl-N-[2-[8-[(tetrahydro-2H-pyran-2-yl)oxy]octyl]-2H-tetrazol-5-yl]-N'-(2,4,6-trimethoxyphenyl)-urea was hydrolyzed to give the title compound. $^1$H NMR ($CDCl_3$): δ 8.6 (br s, 1H), 7.4 (m, 5H), 6.2 (s, 2H), 4.5 (t, 2H), 3.8 (two s, 9H), 3.6 (t, 2H), 2.0 (m, 2H), 1.5 (m, 5H), 1.3 (br s, 6H).

EXAMPLE 15

N'-[2,6-Bis(1-methyl ethyl)phenyl]-N-[2-(8-oxooctyl)-2H-tetrazol-5-yl]-N-phenyl-urea To a stirred, room temperature suspension of pyridinium chlorochromate (0.720 g, 0.00334 mol) and anhydrous sodium acetate (0.0546 g, 0.000666 mol) in dichloromethane (6 mL) was added dropwise over 20 minutes a solution of N'-[2,6-bis(1-methylethyl)-phenyl]-N-[2-(8-hydroxyoctyl)-2H-tetrazol-5-yl]-N-phenyl-urea (1.09 g, 0.00221 mol) in dichloromethane (6 mL), and the mixture was stirred. After 2 hours, diethyl ether (4 mL) was added and the mixture was filtered through celite. The filtercake was washed with dichloromethane. The filtrate and washings were rotoevaporated, and the residue was chromatographed on silica gel (135 g, 230–400 mesh) using PET etherdiethyl ether (1:2, 15–125 mL) as eluent. Fractions containing product were rotoevaporated from dichloromethane to an oil. The oil was dried in vacuo wherein it solidified, yield 0.7108 g (65%) of the title compound, mp=104°–106° C.

EXAMPLE 16

N-[2-(8-Oxooctyl)-2H-tetrazol-5-yl]-N-phenyl-N'-(2.4.6-trimethoxyphenyl)-urea

In a manner similar to Example 15, N-[2-(8-hydroxyoctyl)-2H-tetrazol-5-yl]-N-phenyl-N'-(2,4,6-trimethoxyphenyl)-urea was oxidized to give the title compound. $^1$H NMR ($CDCl_3$): δ 9.8 (t, 1H), 8.6 (br s, 1H), 7.4 (m, 5H), 6.2 (s, 2H), 4.5 (t, 2H), 3.8 (two s, 9H), 2.4 (dr, 2H), 2.0 (m, 2H), 1.6 (m, 2H), 1.3 (br s, 6H).

EXAMPLE 17

N'-[2.6-Bis(1-methylethyl)phenyl]-N-[2-[8-(diethylamino)octyl]-2H=tetrazol-5-yl]-N-phenyl-urea To a room temperature, stirred solution of diethylamine (0.11 mL, 0.0011 mol) in methanol (1.1 mL) was added a 4.8M solution of hydrogen chloride in methanol (0.055 mL, 0.00026 mol HCl), and the solution was stirred. After 10 minutes N'-[2,6-bis(1-methylethyl)-phenyl]-N-[2-(8-oxooctyl)-2H-tetrazol-5-Yl]-N-phenyl-urea (0.4024 g, 0.0008201 mol) was added in one portion, and the mixture was stirred. After 3 minutes the aldehyde had completely dissolved. After 20 minutes, sodium cyanoborohydride (0.0186 g, 0.000296 mol) was added in one portion, and the mixture was stirred. After 40 minutes, a saturated solution of sodium bicarbonate (1.2 mL) was added, and the two-phase mixture was stirred. After 18 hours the mixture was rotoevaporated and the residue was partitioned between water and dichloromethane. The organic layer was dried ($K_2CO_3$) and rotoevaporated to an oil. The oil was chromatographed on silica gel (97 g, 230–400 mesh) using PET ether-diethyl ether (1:1, 7×100 mL) and PET ether-diethyl ethertriethylamine (15:15:2, 13×100 mL) as eluent. Fractions containing product were rotoevaporated from toluene then diethyl ether to give an oil. The oil was dried in vacuo (95° C., 1h) to give the title compound, yield 0.2824 g (63%). $^1H$ NMR ($CDCl_3$): δ 9.2 (br s, 1H), 7.5 (t, 2H), 7.4 (m, 3H), 7.3 (m, 1H), 7.2 (d, 2H), 4.5 (t, 2H), 3.2 (septet, 2H), 2.7 (br s, 4H), 2.6 (m, 2H), 2.0 (m, 2H), 1.6 (m, 2H), 1.3 (m, 8H), 1.2 (d, 12H), 1.1 (br s, 6H).

CHART I (n = 0, $R_2$ aryl, $R_1$ and $R_3$ as defined in Formula I)

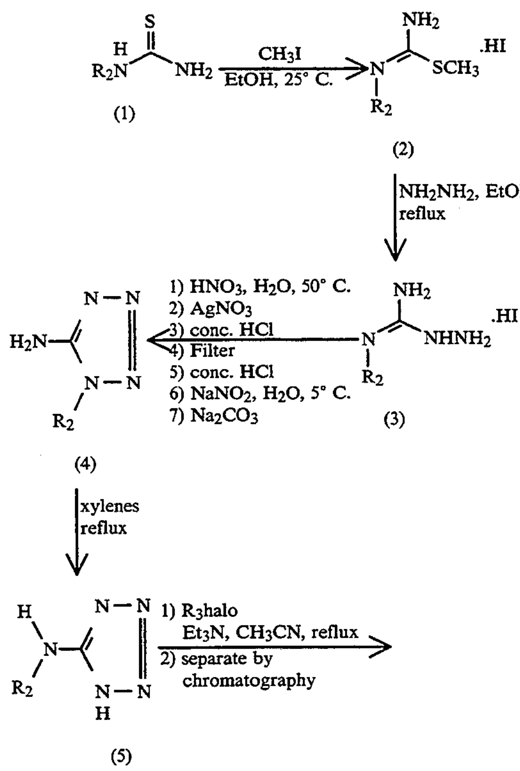

-continued

CHART I

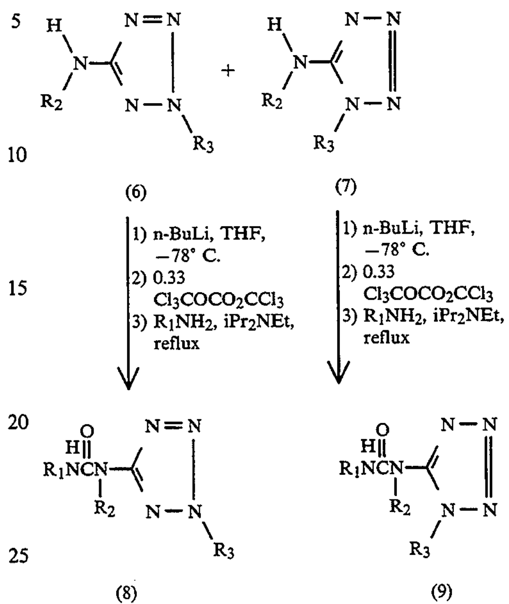

CHART II (n = 0, $R_2$ = cyclohexyl, $R_1$ and $R_3$ are as defined in Formula I)

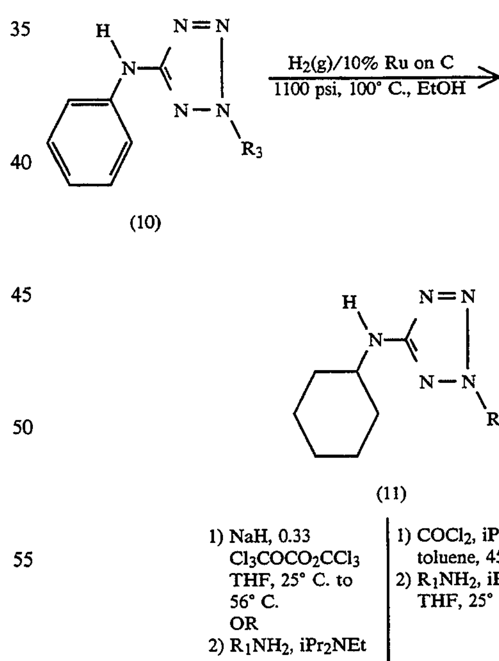

-continued

CHART II

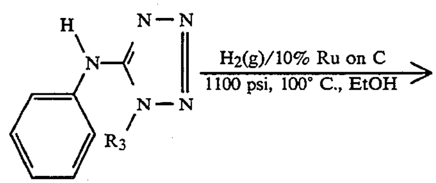

(13)

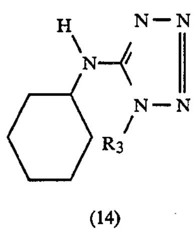

(14)

1) NaH, 0.33 $Cl_3COCO_2CCl_3$ THF, 25° C. to 56° C.
OR
2) $R_1NH_2$, $iPr_2NEt$

1) $COCl_2$, $iPr_2NEt$ toluene, 45° C.
2) $R_1NH_2$, $iPr_2NEt$ THF, 25° C. to 56° C.

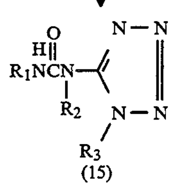

(15)

CHART III (n = 0, $R_2$ = alkyl, cycloalkyl, aralkyl, $R_1$ and $R_3$ are as defined in Formula I)

-continued

CHART III

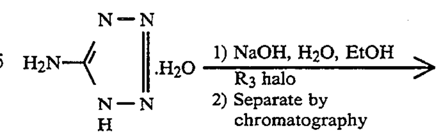

(16)

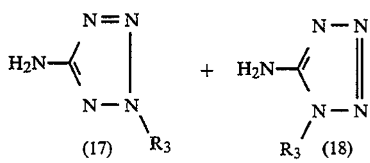

(17) (18)

1) n-BuLi, THF −78° C.
2) $R_2$ halo 25° C.

1) n-BuLi, THF −78° C.
2) $R_2$ halo 25° C.

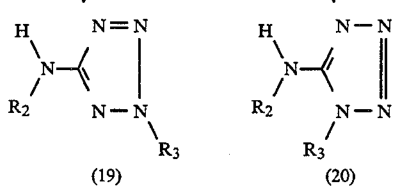

(19) (20)

1) n-BuLi, THF, −78° C.
2) 0.33 $Cl_3COCO_2CCl_3$
3) $R_1NH_2$, $iPr_2NEt$, 25° C.

1) n-BuLi, THF, −78° C.
2) 0.33 $Cl_3COCO_2CCl_3$
3) $R_1NH_2$, $iPr_2NEt$, 25° C.

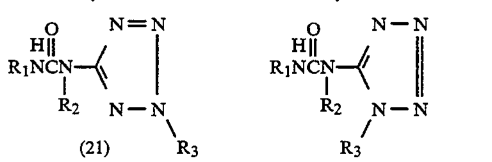

(21) (22)

CHART IV (n = 1 or 2, $R_1$, $R_2$, and $R_3$ are as defined in Formula I)

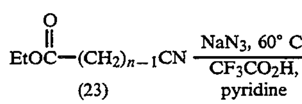

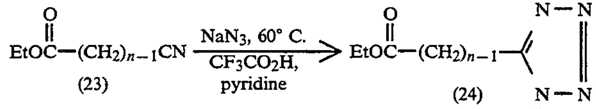

(23) (24)

1) $R_3$ halo, $Et_3N$, $CH_3CN$ reflux
2) Separate by Chromatography

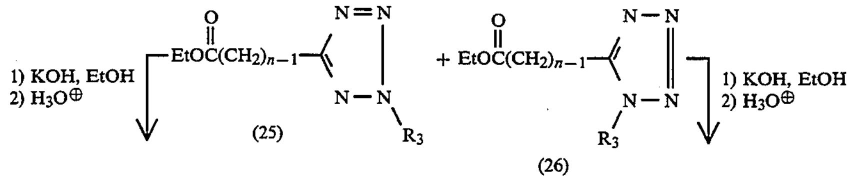

(25) (26)

-continued
CHART IV
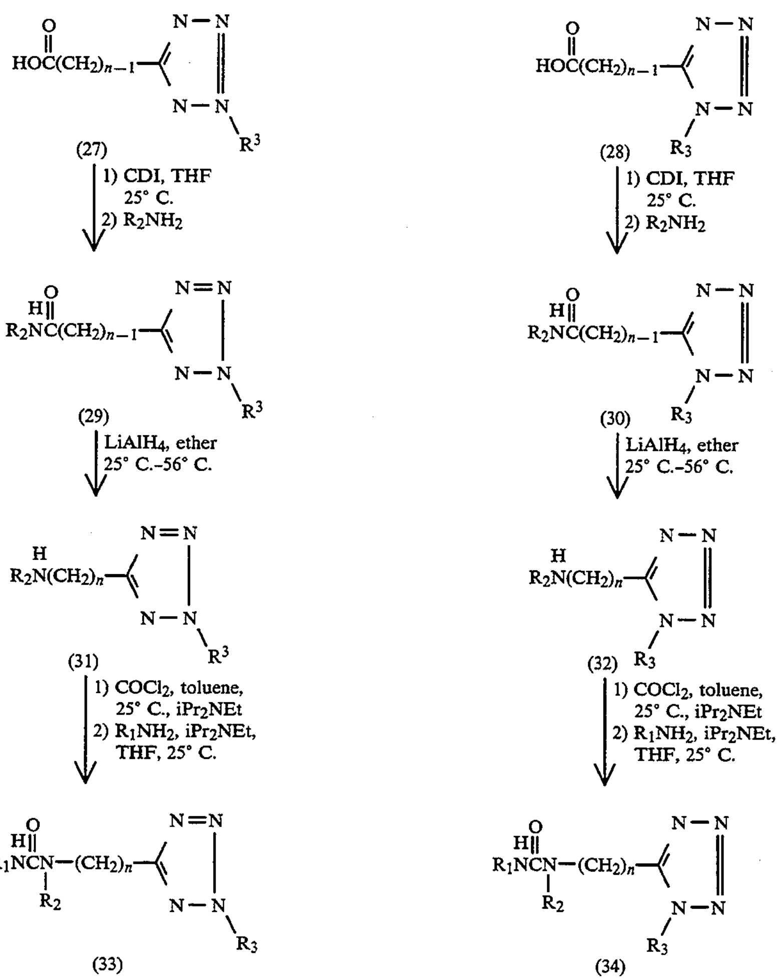
CHART V
($R_3$ is substituted alkyl, n, $R_1$, and $R_2$ are as defined in Formula I)
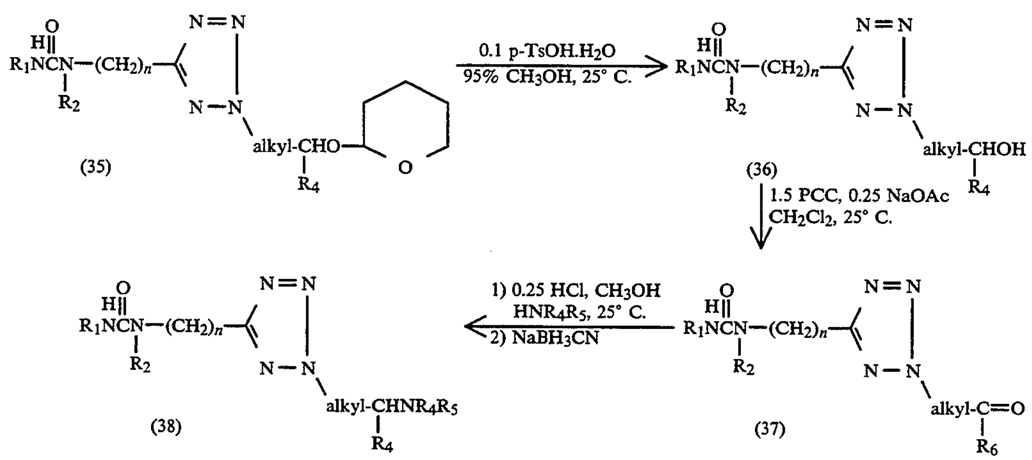

-continued
CHART V
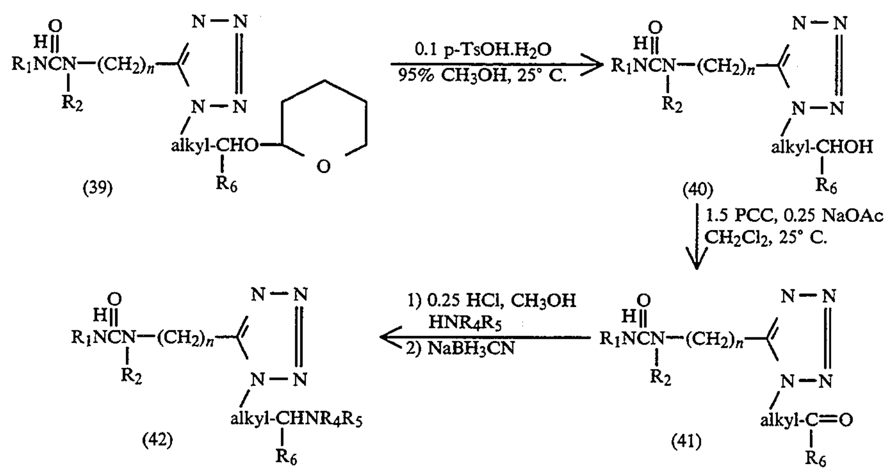
CHART VI
($R_3$ is an alkyl chain of from about 11 to 14 carbon atoms, substituted as shown below, and n, $R_1$, and $R_2$ are as defined in Formula I)
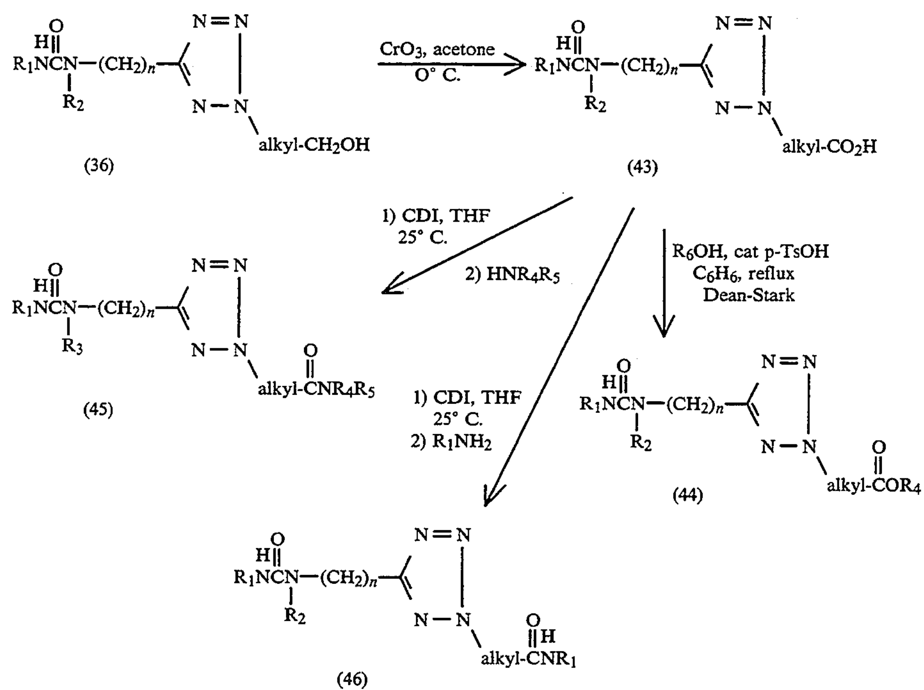
CHART VII
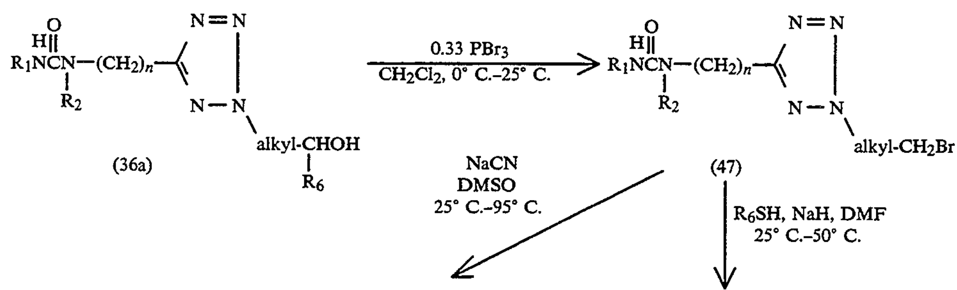

-continued

CHART VII

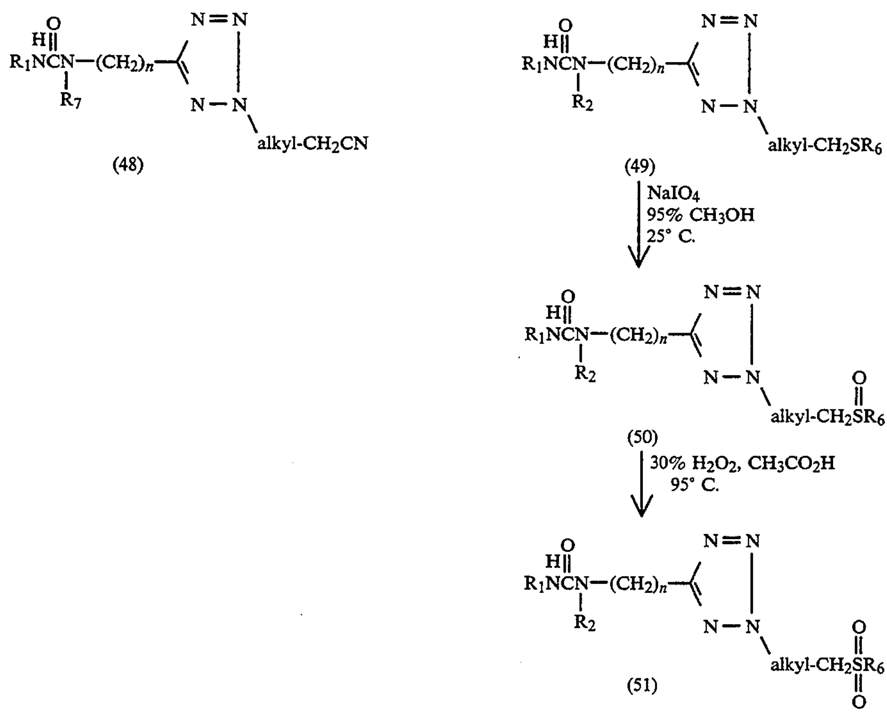

We claim:

1. A compound of the formula

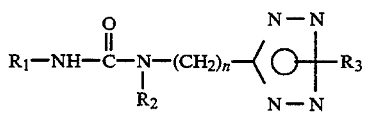

I wherein $R_1$ is phenyl which is unsubstituted or is substituted with from 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

wherein $R_2$ is (a) aryl which is unsubstituted or substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

(b) a straight or branched hydrocarbon group which is saturated or contains from 1 to 3 double bonds and having from 7 to 20 carbon atoms and wherein said group is unsubstituted or is substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

(c) a straight or branched alkoxy group which is saturated or contains from 1 to 3 double bonds and having from 1 to 20 carbon atoms and wherein said group is unsubstituted or is substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms;

(d) a cycloalkyl group having from 3 to 8 atoms which is unsubstituted or substituted with 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms; or (e) aralkyl wherein an aromatic group is attached to a straight or branched alkyl group having from 1 to 4 carbon atoms and which is unsubstituted or is substituted on the aromatic ring with from 1 to 3 substituents selected from fluorine, chlorine, bromine, iodine, hydroxy, a straight or branched alkyl group having from 1 to 6 carbon atoms or a straight or branched alkoxy group having from 1 to 6 carbon atoms;

wherein $R_3$ is attached to either the 1- or 2-position of the tetrazole ring and is selected from a straight or branched hydrocarbon chain having from 1 to 20 carbon atoms and which is saturated or unsaturated containing 1 double bond or 2 or 3 nonadjacent double bonds wherein said chain is unsubstituted or is substituted with from 1 to 6 substituents selected from:

(a) $-NR_4R_5$ wherein each of $R_4$ and $R_5$ is the same or different and is hydrogen, a straight or branched alkyl group having from 1 to 20 carbon atoms or $-NR_4R_5$ taken together form a monocyclic heterocyclic group selected from pyrrolidino, pyridino, piperidino, piperazino, or morpholino, the heterocyclic group being unsubstituted or substituted with a straight or branched alkyl group having from 1 to 4 carbon atoms;

(b) $OR_6$ wherein $R_6$ is hydrogen, a straight or branched alkyl group having from 1 to 20 carbon atoms or a cycloalkyl group having from 3 to 8 carbon atoms or phenyl which is unsubstituted or substituted with from 1 to 3 substituents selected from fluorine, chlorine, bromine, iodine, hydroxy, a straight or branched alkyl group having from 1 to 6 carbon atoms, or a straight or branched alkoxyalkyl group having from 1 to 6 carbon atoms;
(c) $SO_2R_6$ wherein $R_6$ has the meaning defined above;
(d) $SOR_6$ wherein $R_6$ has the meaning defined above;
(e) $SR_6$ wherein $R_6$ has the meaning defined above;
(f) $COR_6$ wherein $R_6$ has the meaning defined above;
(g) $CO_2R_6$ wherein $R_6$ has the meaning defined above;
(h) $CONR_4R_5$ wherein $R_4$ and $R_5$ have the meanings defined above;
(i) $CONHR_1$ wherein $R_1$ has the meaning defined above;
(j) —CHO
(k) —CN
(l) halogen
(m) the group $-(CH_2)r$-phenyl wherein r is 1 to 4 and the phenyl moiety is unsubstituted or is substituted with from 1 to 3 substituents selected from fluorine, chlorine, bromine, iodine, hydroxy, a straight or branched alkyl group having from 1 to 6 carbon atoms, or a straight or branched alkoxy group having from 1 to 6 carbon atoms; or
(n) O-pyranyl which is unsubstituted or substituted with from 1 to 4 substituents selected from fluorine, chlorine, bromine, iodine, hydroxy, a straight or branched alkyl group having from 1 to 6 carbon atoms, or a straight or branched alkoxy group having from 1 to 6 carbon atoms;

and n=0, 1, or 2;

a geometrical or optical isomer, or a pharmaceutically acceptable salt thereof.

2. A compound of claim 1 wherein $R_1$ is substituted phenyl.

3. A compound of claim 1 wherein $R_1$ is di- or trisubstituted phenyl.

4. A compound of claim 1 wherein $R_1$ is 2,4-, 2,6-, or 2,4,6-substituted phenyl.

5. A compound of claim 1 wherein $R_1$ is 2,6-diisopropylphenyl, 2,4,6-trimethoxyphenyl, 2,4-difluorophenyl, or 2,4,6-trifluorophenyl.

6. A compound of claim 1 wherein $R_2$ is phenyl.

7. A compound of claim 1 wherein $R_2$ is substituted phenyl.

8. A compound of claim 1 wherein $R_2$ is 2,4- or 2,4,6-substituted phenyl.

9. A compound of claim 1 wherein $R_2$ is cyclohexyl.

10. A compound of claim 1 wherein $R_2$ is benzyl.

11. A compound of claim 1 wherein $R_3$ is a substituted or unsubstituted straight or branched hydrocarbon chain having from 1 to 20 carbon atoms and which is saturated or unsaturated with 1 double bond or 2 or 3 nonadjacent double bonds.

12. A compound of claim 1 wherein $R_2$ is dodecyl.

13. A compound of claim 1 wherein $R_3$ is on the 2-position of the tetrazole ring.

14. A compound of claim 1 wherein $R_1$ is 2,4- or 2,4,6-substituted phenyl and $R_2$ is phenyl.

15. A compound of claim 14 wherein $R_1$ is 2,6-diisopropylphenyl, 2,4,6-trimethoxyphenyl, 2,4-difluorophenyl, or 2,4,6-trifluorophenyl and $R_2$ is phenyl.

16. A compound of claim 14 wherein $R_3$ is dodecyl.

17. A compound of claim 14 wherein $R_3$ is an 8 carbon alkyl chain substituted at the end with O-tetrahydropyranyl.

18. A compound of claim 1 wherein $R_1$ is 2,4- or 2,4,6-substituted phenyl and $R_2$ is cyclohexyl.

19. A compound of claim 18 wherein $R_3$ is dodecyl.

20. A compound of claim 1 wherein n is 0.

21. A compound of claim 1 which is:

N'-[2,6-bis(1-methylethyl)phenyl]-N-(2-dodecyl-2H-tetrazol-5-yl)-N-phenyl-urea,
N-(2-dodecyl-2H-tetrazol-5-yl)-N-phenyl-N'-(2,4,6-trimethoxyphenyl)-urea,
N'-(2,4-difluorophenyl)-N-(2-dodecyl-2H-tetrazol-5-yl)-N-phenyl-urea,
N'-[2,6-bis(1-methylethyl)phenyl]-N-cyclohexyl-N-(2-dodecyl-2H-tetrazol-5-yl)-urea,
N-cyclohexyl-N-(2-dodecyl-2H-tetrazol-5-yl)-N'-(2,4,6-trimethoxyphenyl)-urea,
N-cyclohexyl-N'-(2,4-difluorophenyl)-N-(2-dodecyl-2H-tetrazol-5-yl)-urea,
N-phenyl-N-(2-tetradecyl-2H-tetrazol-5-yl)-N'-(2,4,6-trimethoxyphenyl)-urea,
N-(2-pentyl-2H-tetrazol-5-yl)-N-phenyl-N'-(2,4,6-trimethoxyphenyl)-urea,
N-(2-dodecyl-2H-tetrazol-5-ylmethyl)-N-(phenylmethyl)-N'-(2,4,6-trimethoxyphenyl)-urea,
(±)N'-[2,6-bis(1-methylethyl)phenyl]-N-phenyl-N-[2-[8-[(tetrahydro-2H-pyran-2-yl)oxy]octyl]-2H-tetrazol-5-yl]-urea,
(±)N-phenyl-N-[2-[8-[(tetrahydro-2H-pyran-2-yl)oxy]octyl]-2H-tetrazol-5-yl]-N'-(2,4,6-trimethoxyphenyl)-urea,
(±)N'-(2,4-difluorophenyl)-N-phenyl-2-[8-[(tetrahydro-2H-pyran-2-yl)oxy]octyl]-2H-tetrazol-5-yl]-urea,
N'-[2,6-bis(1-methylethyl)phenyl]-N-[2-(8-hydroxyoctyl)-2H-tetrazol-5-yl]-N-phenyl-urea,
N-[2-(8-hydroxyoctyl)-2H-tetrazol-5-yl]N-phenyl-N'-(2,4,6-trimethoxyphenyl)-urea,
N'-[2,6-bis(1-methylethyl)phenyl]-N-[2-[8-oxooctyl)-2H-tetrazol-5-yl]-N-phenyl-urea,
N-[2-(8-oxooctyl)-2H-tetrazol-5-yl]-N-phenyl-N'-(2,4,6-trimethoxyphenyl)-urea, or
N'-[2,6-bis(1-methylethyl)phenyl]-N-[2-[8-(diethylamino)octyl]-2H-tetrazol-5-yl]-N-phenyl-urea.

22. A pharmaceutical composition comprising a compound of claim 1 and a pharmaceutically acceptable carrier.

23. A method of treating atherosclerosis in a patient in need of treatment which comprises administering to said patient an effective amount of a compound of claim 1.

* * * * *